(12) United States Patent
Yu et al.

(10) Patent No.: US 8,304,377 B2
(45) Date of Patent: Nov. 6, 2012

(54) SULFONATE SURFACTANTS AND METHODS OF PREPARATION AND USE

(75) Inventors: Wanglin Yu, Midland, MI (US); Cynthia Rand, Sanford, MI (US); Edward D. Daugs, Midland, MI (US); Yang Cheng, Midland, MI (US); Irina V. Graf, Lamesa, TX (US); Andre B. Argenton, Midland, MI (US); Kari S. Phillipson, Hemlock, MI (US)

(73) Assignee: Dow Global Technologies LLC, Midland, MI (US)

( * ) Notice: Subject to any disclaimer, the term of this patent is extended or adjusted under 35 U.S.C. 154(b) by 240 days.

(21) Appl. No.: 12/827,165

(22) Filed: Jun. 30, 2010

(65) Prior Publication Data

US 2011/0015111 A1 Jan. 20, 2011

Related U.S. Application Data

(60) Provisional application No. 61/226,109, filed on Jul. 16, 2009.

(51) Int. Cl.
*C11D 17/00* (2006.01)

(52) U.S. Cl. ......... 510/351; 510/428; 510/429; 510/492

(58) Field of Classification Search ........................ None
See application file for complete search history.

(56) References Cited

U.S. PATENT DOCUMENTS

| | | | |
|---|---|---|---|
| 2,396,278 A | 3/1946 | Lind et al. | |
| 2,486,921 A | 11/1949 | Byerly | |
| 2,486,922 A | 11/1949 | Strain | |
| 2,787,639 A | 4/1957 | Sargent | |
| 2,989,547 A | 6/1961 | Whyte | |
| 3,024,273 A | 3/1962 | Whyte et al. | |
| 3,275,682 A * | 9/1966 | Bakker et al. | 562/111 |
| 4,466,891 A | 8/1984 | McCoy | |
| 4,911,238 A | 3/1990 | Lau et al. | |
| 4,917,823 A | 4/1990 | Maile, Jr. | |

(Continued)

FOREIGN PATENT DOCUMENTS

CH 315882 10/1956

(Continued)

OTHER PUBLICATIONS

Abe et al., "Microemulsion formation with branched tail polyoxyethylene sulfonate surfactants", Journal of Colloid and Interface Science, 1986, vol. 114 No. 2, pp. 342-356, Academic Press.

(Continued)

*Primary Examiner* — Necholus Ogden, Jr.

(57) ABSTRACT

Provided are new anionic surfactants and methods of their preparation and use. The surfactants are compounds of the formula I:

(I)

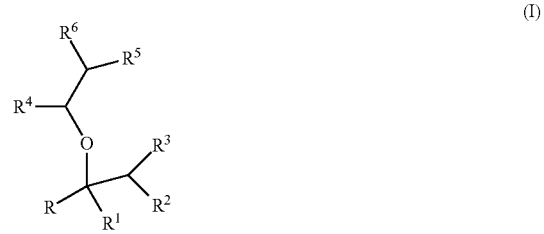

wherein R, $R^1$, $R^2$, $R^3$, $R^4$, $R^5$, and $R^6$ are as defined herein.

9 Claims, 5 Drawing Sheets

U.S. PATENT DOCUMENTS

| | | | |
|---|---|---|---|
| 4,954,281 A | 9/1990 | Resch | |
| 4,976,953 A | 12/1990 | Orr et al. | |
| 5,062,973 A | 11/1991 | Kellett | |
| 5,246,613 A | 9/1993 | Gilbert et al. | |
| 5,620,951 A | 4/1997 | Subramanyam et al. | |
| 5,672,740 A | 9/1997 | Subramanyam et al. | |
| 7,217,834 B2 | 5/2007 | Buding | |
| 2006/0019851 A1 | 1/2006 | Hecht et al. | |
| 2006/0079433 A1 | 4/2006 | Hecht et al. | |
| 2006/0105931 A1 | 5/2006 | Shi et al. | |
| 2006/0105936 A1 | 5/2006 | Shi et al. | |
| 2007/0123446 A1 | 5/2007 | Kenneally et al. | |
| 2008/0009430 A1 | 1/2008 | Hecht et al. | |
| 2009/0281359 A1 | 11/2009 | Daugs et al. | |

FOREIGN PATENT DOCUMENTS

| | | | |
|---|---|---|---|
| EP | 717032 A2 | 6/1996 | |
| EP | 851783 B1 | 12/2006 | |
| WO | 9109924 A1 | 7/1991 | |
| WO | 9740131 A1 | 10/1997 | |

OTHER PUBLICATIONS

Bakker et al., "An Exploratory Study of the Addition Reactions of Ethyleneglycol, 2-Chloroethanol and 1,3-Dichloro-2-Propanol to 1-Dodecene", The Journal of the American Oil Chemists Society, 1967, vol. 44, pp. 517-521.

Bakker et al., "Sulfonates and sulfates of sec-alkyl ethyl ether: detergents prepared by the addition of substituted alcohols to 1-alkenes", Chimi, Physique et Applications Pratiques Des Agents De Surfact, 1968, pp. 157-165.

International Search Report and Written Opinion for PCT/US2010/040570 dated Apr. 20, 2011.

* cited by examiner

SULFONATE SURFACTANTS AND METHODS OF PREPARATION AND USE

This application claims priority to U.S. provisional application Ser. No. 61/226,109, filed Jul. 16, 2009, which is incorporated herein by reference in its entirety.

FIELD OF THE INVENTION

The invention relates to new sulfonate surfactants, compositions of new sulfonate surfactants, and methods of preparation and use of the surfactants.

BACKGROUND OF THE INVENTION

Anionic surfactants are well known and have been used in a variety of applications, including for instance in cleaners and detergents. Common anionic surfactants, such as linear alkylbenzene sulfonate (LAS) and alcohol sulfates (for example sodium lauryl sulfate), however, have poor solubilities in cold water or hard water, and in caustic. So too do alkyl glycerol sulfonate (AGS) surfactants prepared from, for example, epichlorohydrin, a linear alkyl alcohol, and sodium sulfite. This lack of solubility limits the formulation options and the performance of these surfactants.

Providing anionic surfactants with an improved spectrum of properties, such as high solubility in cold, hard, caustic and ionic water while maintaining high surface activity remains a challenge for anionic surfactants.

BRIEF SUMMARY OF THE INVENTION

In one aspect, the invention provides novel anionic sulfonate surfactants. The anionic surfactants are compounds of formula I, or mixtures of two or more thereof:

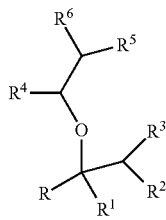

(I)

wherein R, $R^1$, $R^2$, $R^3$, $R^4$, $R^5$, and $R^6$ are as defined below.

In another aspect, the invention provides a formulation containing one or more anionic surfactants of formula I.

In a further aspect, the invention provides cleaning compositions comprising a surfactant of formula I.

In a still further aspect, the invention provides a process for making an anionic surfactant of formula I or mixtures of two or more thereof.

DETAILED DESCRIPTION OF THE INVENTION

Figure 1:
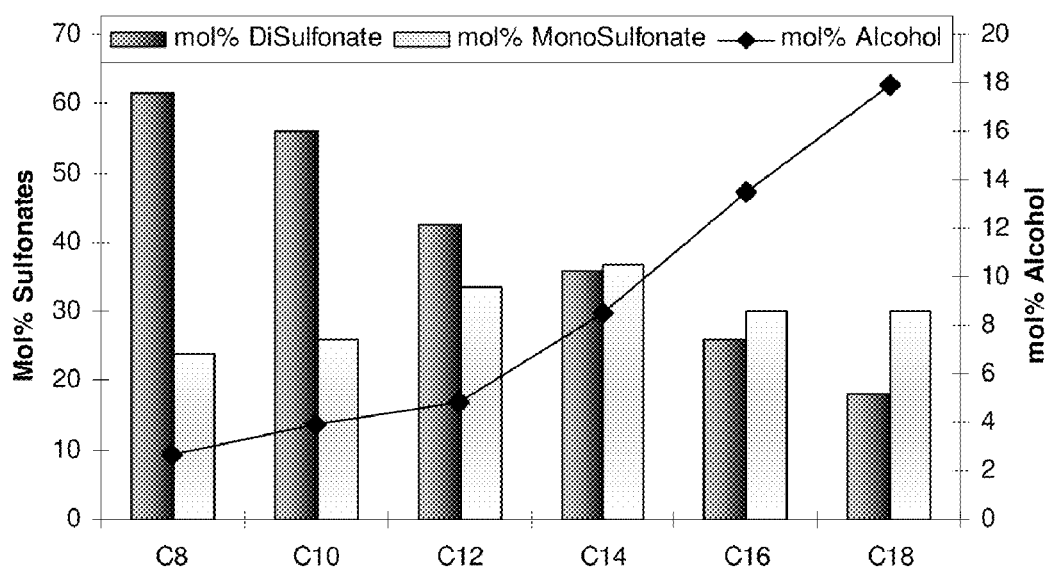
FIG. 1 is a graph showing examples of surfactant compositions that can be obtained through the processes of the invention.

As noted above, in one aspect, the invention provides novel anionic surfactants. An anionic surfactant of the invention contains two sulfonate groups, or one sulfonate and one hydroxy group, on a branched alkyl ether backbone. The anionic surfactants exhibit an improved spectrum of properties relative to other known disulfonate and hydroxy sulfonate (e.g., AGS) surfactants, allowing them to be used in a wide variety of applications. For instance, surfactants of the invention are highly soluble in water, have high tolerance to hard water, electrolytes, and caustic solutions and, when used in cleaning compositions, provide excellent performance in the removal of greasy soils. In addition, as demonstrated by the examples, surfactants of the invention exhibit highly favorable aquatic toxicity.

The anionic surfactants of the invention are compounds of formula I:

(I)

wherein R is linear or branched $C_2$-$C_{22}$ alkyl;
$R^1$, $R^2$, and $R^3$ are independently H or linear or branched $C_1$-$C_{18}$ alkyl;
$R^4$ is H, $CH_2SO_3^-M^+$, or $CH_2OH$;
$R^5$ is OH, $SO_3^-M^+$, or a group of the formula:

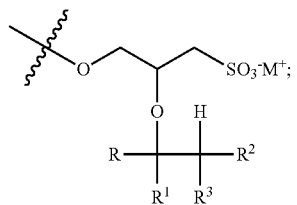

$R^6$ is H, $CH_2SO_3^-M^+$, or $CH_2OH$; and
$M^+$ is $H^+$ or a monovalent or divalent cation, such as sodium, potassium, ammonium, calcium, magnesium, or alkylated ammonium,
wherein one of $R^4$ and $R^6$ is H and wherein one or two of $R^4$, $R^5$, or $R^6$ contains $SO_3^-M^+$.

The processes described below for preparing the surfactants of the invention may result in the formation of mixtures of compounds of formula I. Although the individual compounds of formula I may be isolated from the mixture, this step is not necessary, and indeed it is sometimes preferred that the surfactant be used in the form of the mixture. Thus, surfactants that are mixtures of compounds of formula I are contemplated and are within the scope of the invention.

Preferred surfactants of formula I include compounds of formula I-1 (or mixtures thereof), which are compounds of formula I wherein R is linear $C_2$-$C_{22}$ alkyl. Further preferably, R is linear or branched, more preferably linear, $C_4$-$C_{16}$ alkyl.

Preferred compounds of formulae I and I-1 include compounds of formula I-2, which are compounds of formula I or I-1 wherein $R^1$ is H.

Preferred compounds of formulae I, I-1, and I-2 include compounds of formula I-3, which are compounds of formula I, I-1 or I-2 wherein $R^2$ is H.

Preferred compounds of formulae I, I-1, I-2, and I-3 include compounds of formula I-4, which are compounds of formula I, I-1, I-2 or I-3 wherein $R^3$ is H.

Preferred compounds of formulae I, I-1, I-2, I-3, and I-4 include compounds of formula I-5, which are compounds of formula I, I-1, I-2, I-3, or I-4 wherein $R^4$ is $CH_2SO_3^-M^+$ or $CH_2OH$. In one embodiment, $R^4$ is preferably $CH_2SO_3^-M^+$. In another embodiment, $R^4$ is preferably $CH_2OH$.

Preferred compounds of formulae I, I-1, I-2, I-3, I-4, and I-5 include compounds of formula I-6, which are compounds of formula I, I-1, I-2, I-3, I-4, or I-5 wherein $R^5$ is OH or $SO_3^-M^+$. In one embodiment, $R^5$ is preferably $SO_3^-M^+$. In another embodiment, $R^5$ is preferably OH.

Preferred compounds of formulae I, I-1, I-2, I-3, I-4, I-5, and I-6 include compounds of formula I-7, which are compounds of formula I, I-1, I-2, I-3, I-4, I-5, or I-6 wherein $R^6$ is H.

Preferred compounds of formulae I, I-1, I-2, I-3, I-4, I-5, I-6, and I-7 include compounds of formula I-8, which are compounds of formula I, I-1, I-2, I-3, I-4, I-5, I-6, or I-7 wherein $M^+$ is $H^+$ or a monovalent cation. Further preferably, $M^+$ is $H^+$, $Na^+$, $K^+$, ammonium or alkylated ammonium. Particularly preferred is $Na^+$.

Preferred compounds of formula I further include compounds of formula II:

(II)

wherein R is linear or branched $C_2$-$C_{22}$ alkyl;
$R^1$, $R^2$, and $R^3$ are independently H or linear or branched $C_1$-$C_{18}$ alkyl;
$R^4$ is $CH_2SO_3^-M^+$ or $CH_2OH$;
$R^5$ is OH or $SO_3^-M^+$; and
$M^+$ is $H^+$, or a monovalent or divalent cation, wherein one or both of $R^4$ and $R^5$ contains $SO_3^-M^+$.

Preferred compounds of formula II include compounds of formula II-1, which are compounds of formula II wherein R is linear $C_2$-$C_{22}$ alkyl. Further preferably, R is linear or branched, more preferably linear, $C_4$-$C_{16}$ alkyl.

Preferred compounds of formulae II and II-1 include compounds of formula II-2, which are compounds of formula II or II-1 wherein $R^1$, $R^2$, and $R^3$ are each H.

Preferred compounds of formulae II, II-1, and II-2 include compounds of formula II-3, which are compounds of formula II, II-1, or II-2 wherein $R^4$ is $CH_2SO_3^-M^+$ and $R^5$ is OH.

Preferred compounds of formulae II, II-1, and II-2 include compounds of formula II-4, which are compounds of formula II, II-1, or II-2 wherein $R^4$ is $CH_2SO_3^-M^+$ and $R^5$ is $SO_3^-M^+$.

Preferred compounds of formulae II, II-1, II-2, II-3, and II-4 include compounds of formula II-5, which are compounds of formula III, II-1, II-2, II-3, or II-4 wherein $M^+$ is $H^+$ or a monovalent cation. Further preferably, $M^+$ is $H^+$, $Na^+$, $K^+$, ammonium or alkylated ammonium. Particularly preferred is $Na^+$.

In some embodiments of the invention, the compounds of formula I are of the formula III:

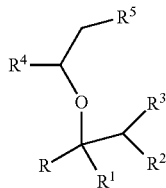

(III)

wherein R is linear or branched $C_2$-$C_{22}$ alkyl;
$R^1$, $R^2$, and $R^3$ are independently H or linear or branched $C_1$-$C_{18}$ alkyl;
$R^5$ is OH or $SO_3^-M^+$;
$R^6$ is $CH_2SO_3^-M^+$ or $CH_2OH$; and
$M^+$ is $H^+$, or a monovalent or divalent cation, wherein one or both of $R^5$ and $R^6$ contains $SO_3^-M^+$.

Preferred compounds of formula III include compounds of formula III-1, which are compounds of formula III wherein R is linear $C_2$-$C_{22}$ alkyl. Further preferably, R is linear or branched, more preferably linear, $C_4$-$C_{16}$ alkyl.

Preferred compounds of formulae III and III-1 include compounds of formula III-2, which are compounds of formula III or III-1 wherein $R^1$, $R^2$, and $R^3$ are each H.

Preferred compounds of formulae III, III-1, and III-2 include compounds of formula III-3, which are compounds of formula III, III-1, or III-2 wherein $R^5$ is OH and $R^6$ is $CH_2SO_3^-M^+$.

Preferred compounds of formulae III, III-1, and III-2 include compounds of formula III-4, which are compounds of formula III, III-1, or III-2 wherein $R^5$ is $SO_3^-M^+$ and $R^6$ is $CH_2OH$.

Preferred compounds of formulae III, III-1, and III-2 include compounds of formula III-5, which are compounds of formula III, III-1, or III-2 wherein $R^5$ is $SO_3^-M^+$ and $R^6$ is $CH_2SO_3^-M^+$.

Preferred compounds of formulae III, III-1, III-2, III-3, III-4, and III-5 include compounds of formula III-6, which are compounds of formula I III, III-1, III-2, III-3, III-4, or III-5 wherein $M^+$ is $H^+$ or a monovalent cation. Further preferably, $M^+$ is $H^+$, $Na^+$, $K^+$, ammonium or alkylated ammonium. Particularly preferred is $Na^+$.

Preferred anionic surfactants of the invention include the compounds shown in Table 1:

TABLE 1

| Name | Structure |
|---|---|
| Sodium 2-hexan-2-yloxypropane-1,3-disulfonate | $NaO_3S\diagdown\diagup SO_3Na$ with O-hexyl group |

TABLE 1-continued

| Name | Structure |
|---|---|
| Sodium 2-hexan-2-yloxy-3-hydroxypropane-1-sulfonate | HO−CH$_2$−CH(O−CH(CH$_3$)−C$_3$H$_7$)−CH$_2$−SO$_3$Na |
| Sodium 2-octan-2-yloxypropane-1,3-disulfonate | NaO$_3$S−CH$_2$−CH(O−CH(CH$_3$)−C$_5$H$_{11}$)−CH$_2$−SO$_3$Na |
| Sodium 2-octan-2-yloxy-3-hydroxypropane-1-sulfonate | HO−CH$_2$−CH(O−CH(CH$_3$)−C$_5$H$_{11}$)−CH$_2$−SO$_3$Na |
| Sodium 2-decan-2-yloxypropane-1,3-disulfonate | NaO$_3$S−CH$_2$−CH(O−CH(CH$_3$)−C$_7$H$_{15}$)−CH$_2$−SO$_3$Na |
| Sodium 2-decan-2-yloxy-3-hydroxypropane-1-sulfonate | HO−CH$_2$−CH(O−CH(CH$_3$)−C$_7$H$_{15}$)−CH$_2$−SO$_3$Na |
| Sodium 2-dodecan-2-yloxypropane-1,3-disulfonate | NaO$_3$S−CH$_2$−CH(O−CH(CH$_3$)−C$_9$H$_{19}$)−CH$_2$−SO$_3$Na |
| Sodium 2-dodecan-2-yloxy-3-hydroxypropane-1-sulfonate | HO−CH$_2$−CH(O−CH(CH$_3$)−C$_9$H$_{19}$)−CH$_2$−SO$_3$Na |
| Sodium 2-tetradecan-2-yloxypropane-1,3-disulfonate | NaO$_3$S−CH$_2$−CH(O−CH(CH$_3$)−C$_{11}$H$_{23}$)−CH$_2$−SO$_3$Na |
| Sodium 2-tetradecan-2-yloxy-3-hydroxypropane-1-sulfonate | HO−CH$_2$−CH(O−CH(CH$_3$)−C$_{11}$H$_{23}$)−CH$_2$−SO$_3$Na |
| Sodium 2-hexadecan-2-yloxypropane-1,3-disulfonate | NaO$_3$S−CH$_2$−CH(O−CH(CH$_3$)−C$_{13}$H$_{27}$)−CH$_2$−SO$_3$Na |

TABLE 1-continued

| Name | Structure |
|---|---|
| Sodium 2-hexadecan-2-yloxy-3-hydroxypropane-1-sulfonate | HO–CH2–CH(O–CH(CH3)–C14H29)–CH2–SO3Na |
| Sodium 2-octadecan-2-yloxypropane-1,3-disulfonate | NaO3S–CH2–CH(O–CH(CH3)–C16H33)–CH2–SO3Na |
| Sodium 2-octadecan-2-yloxy-3-hydroxypropane-1-sulfonate | HO–CH2–CH(O–CH(CH3)–C16H33)–CH2–SO3Na |

In addition to substitution of the alkyl chain at the 2-position as depicted in Table 1, also preferred are structures wherein substitution is at any of the other secondary carbons of the alkyl chain. Further preferred are isomeric mixtures of such compounds.

As discussed above, the processes for preparing the surfactants of the invention may result in the formation of mixtures of compounds of formula I, which can optionally be used directly as surfactants without the need for separation into individual compounds.

By way of example, one preferred mixture comprises: a compound of formula I containing one sulfonate and one hydroxy group; and a compound of formula I containing two sulfonate groups. A further example is a composition comprising a compound of formula II-3, and a compound of formula II-4. FIG. 1 shows additional non-limiting examples.

Another preferred composition comprises an isomeric mixture comprising two or more compounds of formula I wherein the alkyl backbone (formed by R, $R^1$, $R^2$, and $R^3$ and the carbons to which they are attached) is substituted by the ether at least two different secondary carbons.

In another aspect, the invention provides a process for making the anionic surfactants of formula I. In one embodiment, the process comprises:

(a) providing an ether compound of formula A:

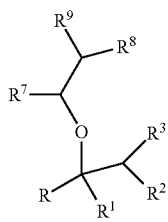

(A)

wherein R, $R^1$, $R^2$, and $R^3$ are as defined above; and
$R^7$ is H or $CH_2X$, $R^8$ is X, and $R^9$ is H or $CH_2X$, wherein one of $R^7$ or $R^9$ is H; and
X is F, Cl, Br, or I (preferably Cl); and (b) sulfonating the ether compound of formula A under sulfonating conditions to provide the compound of formula I.

The ether compound of formula A may be prepared as described in applicants' copending U.S. patent application Ser. No. 12/430,171, filed Apr. 27, 2009 which is incorporated herein by reference in its entirety. Generally, the synthesis comprises the reaction of an alcohol compound with an olefin in the presence of an acidic etherification catalyst. Typically, an equimolar or slight excess of the olefin is used. A solvent may be used, although not required. The reaction may be conducted at elevated temperature, such as about 50 to 150° C. Once the desired amount of the ether compound product is formed (as determined, for instance, by gas chromatography), the reaction mixture is cooled and subjected to conventional workup. For instance, for removal of a homogeneous acid catalyst, the cooled mixture is added to water containing bicarbonate and/or chloride salts, and the organic liquid layer of the mixture containing the ether compound removed. The ether compound may be further purified by known techniques, such as distillation.

The alcohol of the above-described synthesis generally has the following formula:

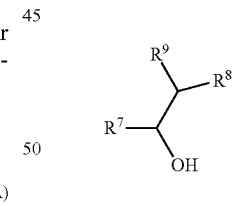

wherein $R^7$, $R^8$, and $R^9$ are as defined above.

Preferred alcohols for the synthesis include: 1,3-dihalo-2-propanol and 2,3-dihalopropanol, or a mixture thereof. Particularly preferred are 1,3-dichloro-2-propanol and 2,3-dichloropropanol, or a mixture thereof.

The olefin for use in the above synthesis is preferably a linear or branched alpha-olefins (i.e., 1-alkenes) containing 4 to 22 carbon atoms, or a mixture of isomers of linear or branched 1-alkenes containing 4 to 22 carbon atoms together with their internal and/or tertiary olefin isomers. Preferably, the alkenes are linear and contain 6 to 18 carbon atoms. Non-limiting examples of particularly preferred alpha olefins include: 1-butene, 1-pentene, 1-hexene, 4-methyl-1-pentene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, or mixtures of two or more thereof.

As the olefin may be isomerized when contacted with the acidic etherification catalyst, it is not necessary to use an alpha-olefin, and internal olefins containing 4 to 22 carbon atoms, or mixtures of isomers of linear or branched alkenes are also suitable for use. Non-limiting examples of suitable internal olefins include: 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene, etc, or mixtures of two or more thereof.

Acidic etherification catalysts suitable for use in the synthesis of the ether compound include, but are not limited to, acidic ionic exchange resins, such as DOWEX DR-2030 available from The Dow Chemical Company, clays, zeolites, sulfonated polystyrene beads, and acids immobilized on a heterogeneous surface, such as tetrafluoroethanesulfonic acid on silica beads, Bronsted acids such as triflic (trifluoromethanesulfonic) acid, methanesulfonic acid, or sulfuric acid, Lewis acids such as $BF_3$ and its derivatives (e.g., dihydrate or ether), and trimethylsilyl triflate. The ratio of catalyst to reactants is not critical and is generally adjusted so as to obtain a desired reaction rate. Preferably, the catalyst is at a temperature of between about 50 and 150° C. during the process in order to facilitate the etherification reaction.

Step (b) of the process is the sulfonation of the ether compound under sulfonating conditions to provide the compound of formula I. Typically, the ether compound is contacted with a sulfonating agent, such as sodium sulfite or combination of sodium sulfite and sodium carbonate. The reaction may be conducted in water and is typically carried out at elevated temperature and pressure, such as 150 to 220° C. and 100 to 350 psig. Following sufficient time for the reaction to occur (e.g., 24 hours), the reaction mixture is cooled and de-pressurized to ambient conditions, and then subjected to conventional workup. The formula I compound may optionally be further purified. Purification may be conducted using conventional techniques, such as extraction, filtration, chromatography, and/or crystallization. If desired, excess sulfite may be oxidized to sulfate by, for example, addition of hydrogen peroxide.

Other typical methods for introducing the sulfonate functionality, such as reaction of the ether compound with a sulfide or polysulfide, then oxidation, may also be used to generate the compounds of formula I.

The anionic surfactants of the invention may be prepared from the difunctional halogenated ether starting material (formula A) as described above. If both halogens are displaced by the sulfonating agent, then the disulfonate compound is formed. If both displacement and hydrolysis takes place, then the hydroxy sulfonate is formed. It should be noted that the hydroxy sulfonate may arise by direct displacement or via the intermediacy of a sultone intermediate that is readily hydrolyzed under the sulfonation conditions, and is therefore not detected in the reaction mixture.

When the anionic surfactant of the invention comprises a mixture of compounds of formula I, the composition of the mixture may be controlled by altering the sulfonation reaction conditions, including alkyl chain length, reaction temperature, basisity, and reagent loadings. In this way, the surfactant product characteristics and properties may be tailored to match the needs of the desired application. A non-limiting example of varying surfactant compositions that may be obtained through the processes of the invention is shown in FIG. 1. The level of by-product alkyl alcohol (i.e. dodecanol in the case of a C12 surfactant example) also formed by hydrolysis is included in FIG. 1.

In addition to preparation from the ether compound of formula A, some of the anionic surfactants of the invention (particularly those containing one sulfonate and one hydroxy group) may also be prepared by analogous processes to those commonly used for making alkyl glyceryl ether sulfonate (AGS) surfactants. Typically, such processes comprise: a) reaction of an alcohol with epichlorohydrin to form an epoxy-compound; and b) sulfonation to form a hydroxy monosulfonate.

The anionic surfactants of formula I may be used in a wide variety of compositions and applications where the presence of surfactants is desired or needed. By way of non-limiting example, the surfactants may be used as or in: laundry detergents, paint and coatings formulations, emulsion polymerization agents or formulations, household and industrial cleaners, agricultural formulations, latex formulations, environmental remediation agents, oilfield chemicals, enhanced oil recovery formulations, gas treating formulations, textile processing and finishing agents, pulp and paper processing agents, fragrance solubilization agents formulations, metal working fluids such as cutting fluids, personal care products (including skin and hair care products such as shampoos), and the like. The amount and composition of the compound of formula I to be used in these applications varies depending on the application and the desired result and can be determined by a person of ordinary skill in the art without undue experimentation. Generally, a composition that includes therein a compound of formula I as a surfactant will contain at least about 0.01 weight percent of the surfactant, based on the total weight of the composition.

In a preferred embodiment, the surfactants of formula I are used in cleaning compositions, such as laundry detergents. One of the problems currently experienced with cleaning compositions by industry and consumers is the lack of efficiency in the removal of greasy soils. This lack of efficiency is even more pronounced when cleaning is carried out at room temperature and/or in the presence of hard water. Another problem is the instability of anionic surfactants in the presence of metal ions, such as calcium and magnesium.

The anionic surfactants of formula I address the foregoing problems. In particular, the surfactants provide excellent performance in the removal of greasy soils and are soluble in the presence of calcium and magnesium ions. In addition to greasy soils, cleaning compositions containing the surfactants of the invention may also be used to remove other types of soiling including, but not limited to, particulate soils, oxidizable soils, organic and inorganic soils.

The amount of the surfactant of formula I that should be used in a cleaning composition can be easily determined by a person of ordinary skill in the art. By way of example, the amount is typically from about 0.01% to 30%, preferably 1% to 20%, by weight based on the total weight of the cleaning composition. In actual use, such as in laundry applications, it is generally preferred that the cleaning composition be diluted with water before or during the washing time to provide a concentration ranging from 0.01% to 5%, preferably from 0.01% to 1% and more preferably from 0.01% to 0.5% by weight of the formula I surfactant.

Cleaning compositions may optionally contain other additives commonly used in such compositions including, for instance, one or more additives selected from: other anionic surfactants, non ionic surfactants, cationic surfactants, amphoteric surfactants, enzymes, solvents, hydrotropes, builders, thickening agents, chelating agents, perfume, dyes, opacifiers, optical brighteners, bleaching agents, and pH buffers. Buffers are typically used in order to maintain a preferred pH in the composition between 4 and 14.

When present, the amounts of such optional additives are preferably as follows: anionic surfactants in the range of 0.01% to 50%, preferably from 0.01% to 25%, more preferable, 1% to 20%; non ionic surfactants in the range of 0.01% to 20%, preferably from 0.01 to 15% more preferably from 0.5% to 10%; cationic surfactants in the range of 0.01% to 20%, preferably from 0.01 to 15% more preferably from 0.5% to 10%; amphoteric surfactants in the range of 0.01% to 20%, preferably from 0.01 to 15% more preferably from 0.5% to 10%; enzymes in the range of 0.0001% to 6%; solvents in the range of 0.01% to 20%, preferably from 0.01 to 15% more preferably from 0.5% to 10%; builders in the range of 1% to 60%; chelating agents in the range of 0.1% to 20%; and hydrotropes in the range of 0.1% to 15%, preferable from 0.5% to 10%.

As noted above, the invention provides new anionic surfactants that exhibit an improved spectrum of properties, allowing them to be used in a wide variety of applications. Such properties include low aquatic toxicity, high solubility in water, high tolerance to hard water, electrolytes, and caustic solutions, and, when used in cleaning compositions, excellent performance in the removal of greasy soils.

The following examples are illustrative of the invention but are not intended to limit its scope. Unless otherwise indicated, the ratios, percentages, parts, and the like used herein are by weight.

EXAMPLES

Example 1

Etherification of Alpha-olefin with 1,3-Dichloro-2-propanol

Exemplary ether compounds, precursors to the compounds of formula I, may be prepared by the following protocol.

A bottom-drain Dean-Stark trap with a glass wool plug to retain the resin beads is charged with 16.2 g of DOWEX DR-2030 resin, the resin is wetted with 11.5 g of 1,3-dichloro-2-propanol, and the apparatus attached to a 1-L round bottom flask. The flask is charged with 1.1 mol of an alpha-olefin and 139.7 g of 1,3-dichloro-2-propanol (total of 1.17 mol). Vacuum is applied, and the 1-L flask heated such that distillate from the 1-L flask is condensed into the Dean Start trap containing the warmed resin, and returned to the 1-L flask. The temperature in the 1-L flask climbs with continued distillation. The reaction mixture is purified by distillation to afford alkyl 1,3-dichloropropyl ether.

Example 2

Preparation of Sulfonates with Sodium Sulfite/meta-Bisulfite

Exemplary surfactants of the invention can be made by the following protocol.

A 2 L Parr reactor is charged with 0.456 mol of the alkyl 1,3-dichloropropyl ether (from Example 1), 0.783 mol of sodium sulfite, 0.180 mol of sodium meta-bisulfite, 0.289 mol of sodium carbonate, and 590 g of water. Following a nitrogen flush and pressure check, the system is heated to 200° C. for 20 hours. The pressure after reaching temperature is 250 psig. The solution is cooled to ambient temperature and unloaded to afford the reaction product.

Example 3

Etherification of 1-Dodecene with 1,3-Dichloro-2-propanol

An ether made substantially according to the protocol described in Example 1 was produced as follows. A 2-L reactive distillation apparatus was constructed as described here. A 2-L round-bottom flask with a magnetic stirrer was fitted into a heating mantle and connected to a distillate receiver. Distillate was condensed into the side arm distillate receiver containing a magnetic stirrer and temperature probe. A valved line between the distillate receiver and the 2-L flask gave a nominal volume of about 100 mL in the distillate receiver. Liquid was pumped from the bottom of the distillate receiver to a 21 inches long and ¾ inches in diameter stainless steel tube fitted on each end with 90 μm screen filters to provide a catalyst bed. A jacket system covering the catalyst containing pipe was heated using a recirculating hot oil bath. The outlet of the catalyst bed returned liquid to the distillate receiver. The system was connected to a vacuum pump such that the reactive distillation could be carried out at pressures of 10 to 300 torr. The catalyst bed of the 2-L reactive distillation apparatus was charged with 60 g of DOWEX DR-2030. The 2-L vessel was charged with 684.72 g (5.304 mol) of 1,3-dichloro-2-propanol and 843.05 g (5.009 mol) of 1-dodecene. The vacuum was adjusted to 22 torr, and the 2-L vessel was heated to afford distillation at an initial temperature of 79° C., with a vapor temperature of 70° C. The catalyst bed oil bath was set to 110° C. to give a temperature in reaction product exiting the catalyst bed of 80-88° C. The condenser temperature was about −11° C. to −5° C. The distillate receiver temperature was 63 to 69° C. With additional heating, the bottoms temperature reached 192° C. and the overhead temperature was 80° C. The mixture was cooled and unloaded. The solution in the distillate receiver and catalyst bed (96.30 g, 6.3% of mass loaded) was discarded. The solution in the 2-L vessel (1302.33 g, 85.2% of mass loaded) was analyzed by GC analysis (1.803 area %, 1.10 wt % of dodecene, 0.708 area %, 0.48 wt % of dodecanol, 0.01 area %, 0.03 wt % of 1,3-dichloro-2-propanol, 89.843 area %, 88.71 wt % of the C12 1,3-dichloropropyl ether). A portion (1298.01) was loaded to a 2-L round-bottom flask and purified by distillation at 0.2 to 0.6 torr using a 14" vacuum-jacketed Vigreux column topped with a reflux splitter. The first fraction (30.36 g) was collected using a 15:1 reflux ratio at an overhead temperature of 25 to 105° C. with a bottoms temperature of 146-189° C. The product fraction was collected using a 15:1 reflux ratio at an overhead temperature of 104 to 118° C. with a bottoms temperature of 190-220° C. to afford 1217.88 g (4.09 mol) of the 1,3-dichloropropyl ether of dodecane (1,3-dichloropropan-2-lyoxydodecane, 94.8 area % C12 DCP ether, mixture of positional isomers, 93.8% distilled yield). A 42.10-g residue remained as the distillation bottoms.

Example 4

Preparation of C6 Sulfonate Reaction Product with Aqueous Sodium Sulfite

A 2 L Parr reactor was charged with 44.48 g (0.209 mol) of 1,3-dichloropropan-2-yloxyhexane, prepared essentially as described in Example 3 using appropriate substitutions for starting materials, 68.7 g (0.545 mol) of sodium sulfite, 3.06 g (0.029 mol) of sodium carbonate, and 251.25 g of de-ionized water. Following a nitrogen flush and pressure check, the system was heated to 170° C., for 24 hours. The resulting pressure was 130 psig. The solution was cooled to ambient temperature to afford 338.69 g of solution. The solution was extracted with ethyl acetate (173.7, then 45.0 g) and the combined upper ethyl acetate phases evaporated to a residue of 1.59 g. GC analysis of the residue found that it contained 18 wt % of C6 1,3-dichloro-2-propanol ether. The aqueous solution was filtered and partially concentrated to afford 267.95 g of solution. NMR analysis found 17 wt % (0.135 mol, 65% of theory) of sodium 2-(hexyloxy)propane-1,3-disulfonate (C6 Disulfonate) and 2.6 wt % (0.026 mol, 12% of theory) of sodium 2-(hexyloxy)-3-hydroxypropane-1-sulfonate (C6 Monosulfonate).

Example 5

Preparation of C8 Sulfonates with Sodium Sulfite/meta-Bisulfite

A surfactant of the invention made substantially according to the protocol described in Example 2 was produced as follows. A 2 L Parr reactor was charged with 156.0 g (0.646 mol) of 1,3-dichloropropan-2-yloxyoctane, prepared substantially as described in Example 3 using appropriate substitutions of starting materials, 137.1 g (1.09 mol) of sodium sulfite, 48.1 g (0.253 mol) of sodium meta-bisulfite, 53.88 g (0.508 mol) of sodium carbonate, and 600.0 g of water. Following a nitrogen flush and pressure check, the system was heated to 180° C. for 20 hours. The pressure was 150 psig at temperature, and rose to 190 psig overnight. The solution was cooled to ambient temperature and unloaded to afford 944.18 g of light brown reaction product with a brown oil layer on top. The pH was 7.14. HPLC analysis of the aqueous solution found 15.3 wt % (0.381 mol, 59.0% of theory) of C8 Disulfonate (sodium 2-(octyloxy)propane-1,3-disulfonate) and 4.1 wt % (0.206 mol, 21% of theory) of C8 Monosulfonate (sodium 2-(octyloxy)-3-hydroxypropane-1-sulfonate). A 24.70-g portion of the entire reaction product was removed and extracted with 12.73 g of ethyl acetate. GC assay of the 11.55-g organic phase found 0.418 wt % of octanol (1.88 g in 944.18 g of solution, 0.0119 mol, 1.8 mol % of C8 1,3-dichloro-2-propanol ether charged) and 3.75 wt % of the C8 1,3-dichloro-2-propanol ether and the C8 olefin dimer product (hexadecene isomers) (16.9 g in 944.18 g of solution, 10.8 wt % of C8 1,3-dichloro-2-propanol ether charged).

Example 6

Preparation of C10 Sulfonates with Sodium Sulfite/meta-Bisulfite

The compounds were made substantially according to the protocols described above, using appropriate substitutions of starting materials (138.6 g of 1,3-dichloro-2-propan-2-yloxydecane, 112.5 g of sodium sulfite, 39.0 g of sodium meta-bisulfite, 34.52 g of sodium carbonate, 550.43 g of water, 190° C., 20 hours). Following reaction, the reaction mixture was cooled to ambient temperature and unloaded to afford 826.5 g of light brown reaction product. The pH was 7.11. HPLC analysis of the aqueous solution found 14.3 wt % (0.292 mol, 56.6% of theory) of C10 Disulfonate (sodium 2-(decyloxy)propane-1,3-disulfonate) and 5.4 wt % (0.139 mol, 27.0% of theory) of C10 Monosulfonate (sodium 2-(decyloxy)-3-hydroxypropane-1-sulfonate). A 18.44-g portion was removed and extracted with 6.45 g of ethyl acetate. GC assay of the 5.06-g organic phase found 0.662 wt % of decene (1.50 g in 826.5 g of solution, 1.1% of C10 1,3-dichloro-2-propanol ether charged), 1.44 wt % of decanol (3.26 g in 826.5 g of solution, 0.0206 mol, 4.0 mol % of C10 1,3-dichloro-2-propanol ether charged), 1.15 wt % of the C10 1,3-dichloro-2-propanol ether (2.60 g in 826.5 g of solution, 1.9% of C10 1,3-dichloro-2-propanol ether charged), and 0.615 wt % of the C10 olefin dimer product eicosene (1.39 g in 826.5 g of solution, 1 wt % of C10 1,3-dichloro-2-propanol ether charged).

Example 7

Preparation of C12 Sulfonates with Sodium Sulfite/meta-Bisulfite

The compounds were made substantially according to the protocols described above, using appropriate substitutions of starting materials (135.5 g of 1,3-dichloro-2-propan-2-yloxydodecane, 98.66 g of sodium sulfite, 34.18 g of sodium meta-bisulfite, 30.66 g of sodium carbonate, 590 g of water, 200° C., 20 hours). Following reaction, the reaction mixture was cooled to ambient temperature and unloaded to afford 865.3 g of light brown reaction product. The pH was 7.75. HPLC analysis of the aqueous solution found 9.14 wt % (0.183 mol, 40% of theory) of sodium 2-(dodecanyloxy)propane-1,3-disulfonate (C12 Disulfonate) and 5.69 wt % (0.142 mol, 31% of theory) of sodium 2-(dodecanyloxy)-3-hydroxypropane-1-sulfonate (C12 Monosulfonate). A 10.4-g portion was removed and extracted with 4.00 g of ethyl acetate. GC assay of the 2.77-g organic phase found 0.2 wt % of dodecene (0.46 g in 865.3 g of solution, 0.34% of C12 1,3-dichloro-2-propanol ether charged), 1.98 wt % of dodecanol (4.56 g in 865.3 g of solution, 0.0245 mol, 5.4 mol % of C12 1,3-dichloro-2-propanol ether charged), and 1.35 wt % of the C12 1,3-dichloro-2-propanol ether (3.11 g in 865.3 g of solution, 2.3% of C12 1,3-dichloro-2-propanol ether charged).

Example 8

Preparation of C14 Sulfonates with Sodium Sulfite/meta-Bisulfite

The compounds were made substantially according to the protocols described above, using appropriate substitutions of starting materials (160.8 g of 1,3-dichloro-2-propan-2-yloxytetradecane, 108.53 g of sodium sulfite, 37.46 g of sodium meta-bisulfite, 35.14 g of sodium carbonate, 828.5 g of water, 203° C., 20 hours). Following reaction, the reaction mixture was cooled to ambient temperature and unloaded to afford 1156.0 g of yellow reaction product. The pH was 6.67. HPLC analysis of the aqueous solution found 7.19 wt % (0.181 mol, 37% of theory) of C14 Disulfonate (sodium 2-(tetradecyloxy)propane-1,3-disulfonate) and 5.70 wt % (0.176 mol, 36% of theory) of C14 Monosulfonate (sodium 2-(tetradecyloxy)-3-hydroxypropane-1-sulfonate). A 19.80-g portion was removed and extracted with 8.76 g of ethyl acetate. GC assay of the 7.06-g organic phase found 0.29 wt % of tetradecene (1.18 g in 1156 g of solution, 0.73% of C14 1,3-dichloro-2-propanol ether charged), 1.99 wt % of tetradecanol (8.2 g in 1156 g of solution, 0.0383 mol, 7.7 mol % of C14 1,3-dichloro-2-propanol ether charged), and 1.53 wt % of the C14 1,3-dichloro-2-propanol ether (6.3 g in 1156 g of solution, 3.9% of C14 1,3-dichloro-2-propanol ether charged).

Example 9

Preparation of C16 Sulfonates with Sodium Sulfite/meta-Bisulfite

The compounds were made substantially according to the protocols described above, using appropriate substitutions of starting materials (87.10 g of 1,3-dichloro-2-propan-2-yloxyhexadecane, 53.57 g of sodium sulfite, 19.83 g of sodium meta-bisulfite, 19.11 g of sodium carbonate, 558.44 g of water, 207° C., 31 hours). Following reaction, the reaction mixture was cooled to ambient temperature and unloaded to afford 677 g of an emulsified product mixture (91.7% of mass loaded). A portion of the emulsion remained on the walls of the reactor. HPLC analysis of the clear solution provided by dilution of a 9.5891-g portion with 86.30 g of water found 3.39 wt % of C16 Disulfonate (sodium 2-(hexadecyloxy)propane-1,3-disulfonate (corresponding to 0.051 mol in the 738-g product solution, or 20.8 mol %) and 4.74 wt % of C16 Monosulfonate (sodium 2-(hexadecyloxy)-3-hydroxypropane-1-sulfonate) (corresponding to 0.087 mol in the 738-g product solution, or 35.3 mol %). Dilution of a 38.41-g portion of the product mixture with 19.04 g of ethyl acetate gave two clear phases. A GC assay of the top 16.80-g organic phase found 0.619 wt % of hexadecene (2.0 g in the 738-g reaction product solution, 2.3% of C16 1,3-dichloro-2-propanol ether charged), 2.28 wt % of hexadecanol (7.35 g in the 738-g reaction product solution, 0.0303 mol, 12.2 mol % of C16 1,3-dichloro-2-propanol ether charged), and 0.57 wt % of the C16 1,3-dichloro-2-propanol ether (1.85 g in the 738-g reaction product solution, 2.1% of C16 1,3-dichloro-2-propanol ether charged).

Example 10

Preparation of C18 Sulfonates with Sodium Sulfite/meta-Bisulfite

The compounds were made substantially according to the protocols described above, using appropriate substitutions of starting materials (107.36 g of 1,3-dichloro-2-propan-2-yloxyoctadecane, 62.2 g of sodium sulfite, 21.74 g of sodium meta-bisulfite, 21.08 g of sodium carbonate, 584.7 g of water, 212° C., 24 hours). Following reaction, the reaction mixture was cooled to ambient temperature and unloaded to afford 607.54 g of a very thick white emulsion (76.2% of mass loaded). A portion of the emulsion remained on the walls of the reactor. Dilution of a 281.55-g portion of the product mixture with 307.14 g of ethyl acetate and 254 g of water gave two clear phases. The top organic phase (288.25 g) was evaporated to a residue of 13.36 g. GC assay of the organic residue found 9.97 wt % of octadecene (3.79 g in the 797-g reaction product, 3.5% of C18 1,3-dichloro-2-propanol ether charged), 36.32 wt % of octadecanol (13.81 g in the 797-g reaction product, 0.0504 mol, 17.9 mol % of C18 1,3-dichloro-2-propanol ether charged), and 47.52 wt % of the C18 1,3-dichloro-2-propanol ether (18.1 g in the 797-g reaction product, 16.8% of C18 1,3-dichloro-2-propanol ether charged). A 5.50-g portion of the reaction product was diluted with 44.16 g of water, and 5.34 g of 2-propanol to give a hazy solution (1:10 dilution). HPLC analysis of the solution found that the reaction product contained 3.25 wt % of C18 Disulfonate (sodium 2-(octadecyloxy)propane-1,3-disulfonate) (corresponding to 0.0501 mol in the 797-g product solution, or 17.8 mol %) and 4.47 wt % of C18 Monosulfonate (sodium 2-(octadecyloxy)-3-hydroxypropane-1-sulfonate) (corresponding to 0.0828 mol in the 797-g product solution, or 29.5 mol %).

Example 11

Isolation of Individual Surfactant Components

The individual surfactant components may be isolated from the sulfonate compositions of the invention. For example, the C12 sulfonate composition of Example 7 is charged to a column containing a C18 reverse phase chromatography resin and eluted with an aqueous solution of acetonitrile. Fractions containing the desired components are collected and evaporated to provide isolated solid samples of sodium 2-(dodecanyloxy)propane-1,3-disulfonate (C12 Disulfonate) and sodium 2-(dodecanyloxy)-3-hydroxypropane-1-sulfonate (C12 Monosulfonate).

Example 12

Surface Tension Evaluation

Figure 2:
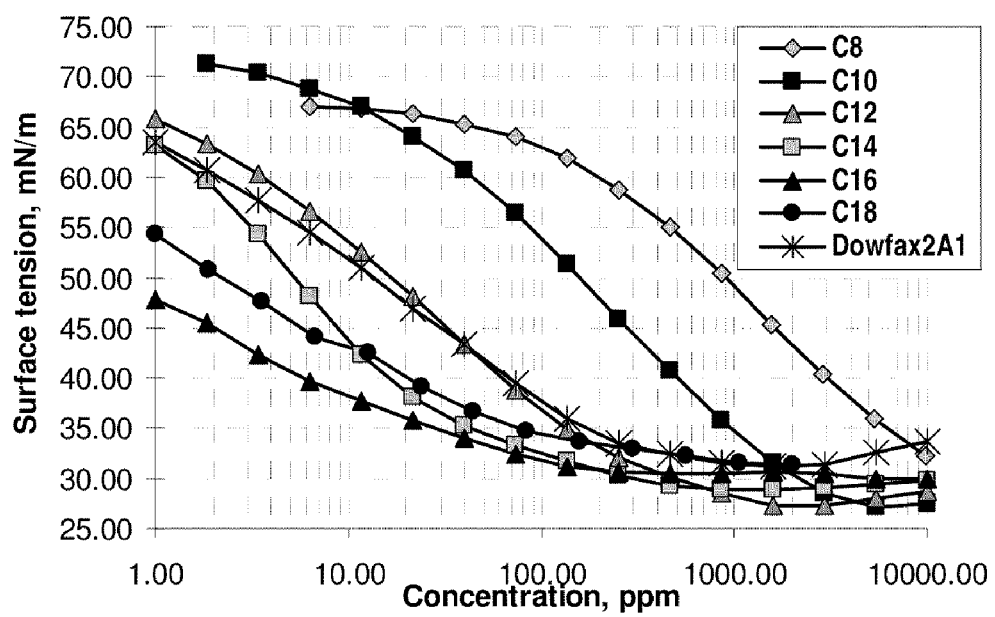
FIG. 2 is a graph showing surface tension results for anionic surfactants of the invention compared with a non-inventive surfactant.

The surface tension is measured by the Wilhelmy plate using a Kruss K100 tensiometer. A reverse CMC extended method is utilized. In this method, the surfactant solution is first put into the sample vessel and then diluted with the deionized water stepwise. After each water addition, the sample is stirred, then the same amount of solution is removed, keeping a constant volume. Surface tension analysis results for the C8 to C18 sulfonate compositions of the invention, as produced in Examples 5-10, in 0.1 M sodium chloride, as compared to alkyldiphenyloxide disulfonate (available as DOWFAX™ 2A1 from The Dow Chemical Company) are shown in the FIG. 2. Results indicate that these sulfonated materials of the invention show good surfactancy, as they achieve a low surface tension (below 30 mN/m), and in case of the C14 and C16 Sulfonates, reach minimum surface tensions at lower concentrations than Dowfax 2A1, with CMC of 68 mN/m and 74 mN/m respectively, as opposed to 232 mN/m for Dowfax 2A1.

Example 13

Dynamic Surface Tension Evaluation

Dynamic surface tensions for 1 wt % surfactant solutions are measured utilizing a Kruss Bubble Pressure Tensiometer BP2, that measures the dynamic surface tension of liquids using the maximum bubble pressure method. Dynamic surface tension is a key property of a surfactant, as it indicates how quickly the surfactant molecules migrate to the interface, and thus, how effectively surfactants reduce surface tension within the application timescale.

Figure 3:
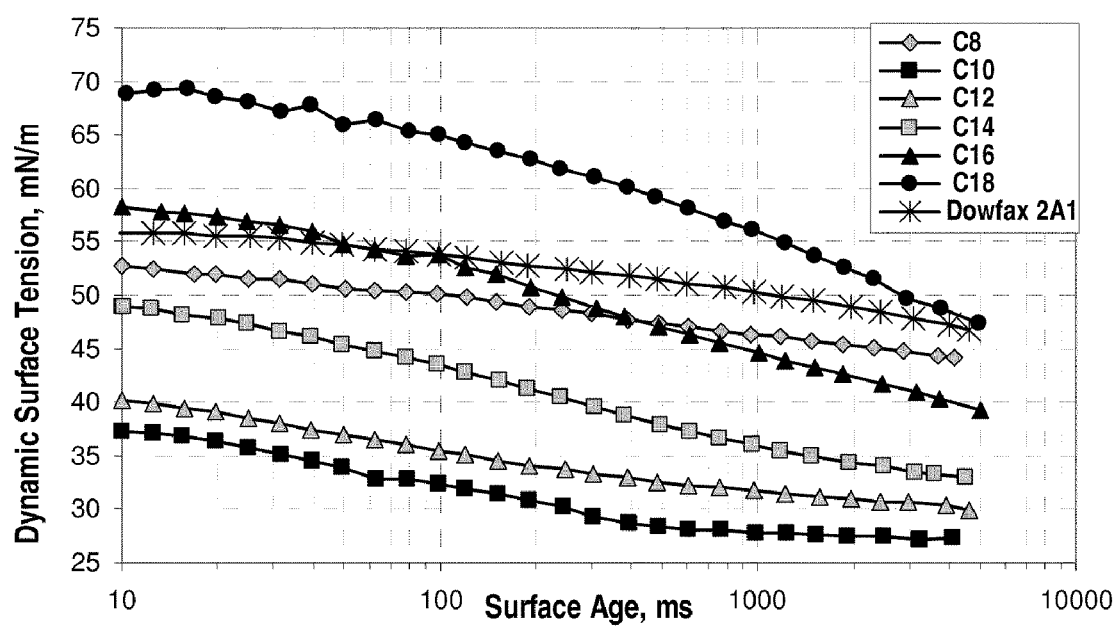
FIG. 3 is a graph showing dynamic surface tension results for anionic surfactants of the invention compared with a non-inventive surfactant.

Dynamic surface tension for the C8 to C18 sulfonate compositions of the invention, as produced in Examples 5-10, indicate that these surfactants migrate to interface faster than DOWFAX™ 2A1 (FIG. 3). This may be a critical advantage for dynamic processes, such as inkjet printing, for example.

Example 14

Foaming Evaluation

Figure 4:
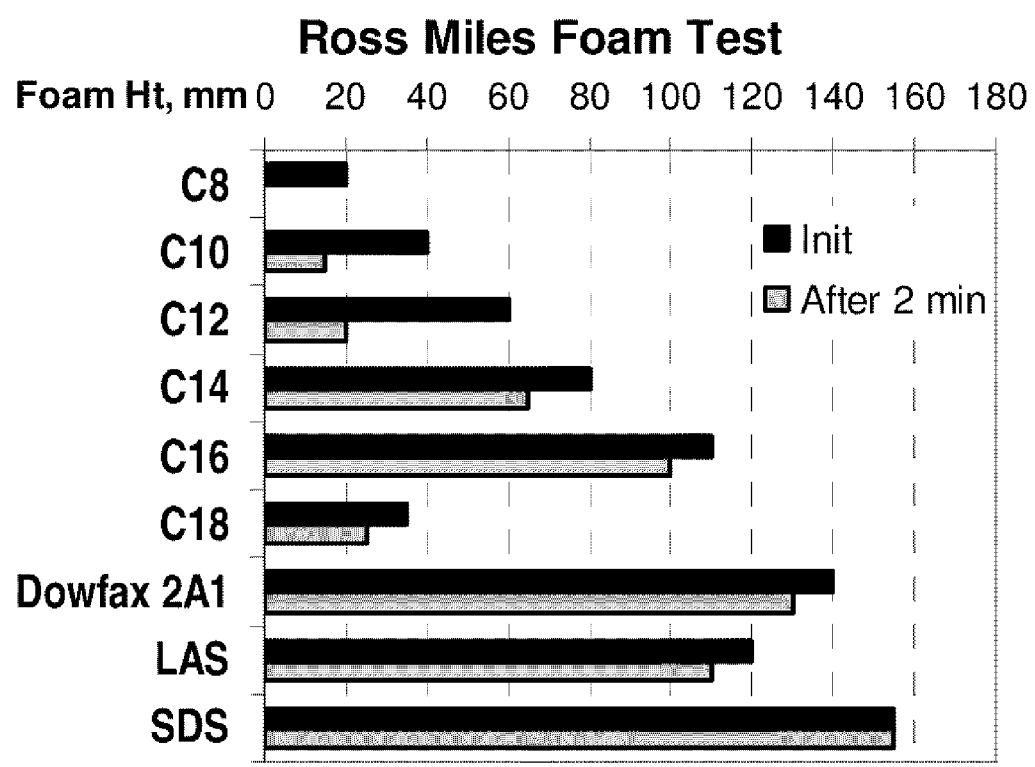
FIG. 4 is a graph showing Ross-Miles foaming test results for anionic sufactants of the invention compared with a non-inventive surfactant.

A Ross-Miles Foam Test is conducted in accordance with ASTM method D 1173 using 0.1 wt % surfactant solutions. Ross-Miles foaming test results for the C8 to C18 sulfonate compositions of the invention, as produced in Examples 5-10, as compared to DOWFAX™ 2A1 are shown in the FIG. 4. Results are expressed as the height of foam at initial pour time, and after 2 minutes. Surfactants which produce less than 40 mm foam height, or break to 40 mm after 2 minutes are considered low foam surfactants, while surfactants producing over 120 mm foam heights are considered to be high foam surfactants. Surfactant applications often have specific foaming needs and/or limitations. Foaming results show application potential for both low foam or high foam requirements can be met with the surfactants of the invention, depending on the hydrophobe composition.

Example 15

Solubility Evaluation

For solubility evaluations in aqueous caustic, 2 ml of 1% surfactant solution are combined with 8 ml of deionized water and mixed well by hand-shaking the vial; 10 ml of 20% NaOH solution is then added, and the sample vial shaken for 30 seconds. The final concentrations are: 0.1 wt % for surfactant, 10 wt % for NaOH.

For solubility evaluations with calcium chloride, 2 ml of 1% surfactant solution are combined with 8 ml of deionized water and mixed well by hand-shaking the vial; 10 ml of 2 M $CaCl_2$ solution is then added, and the sample vial shaken for 30 seconds. The final concentrations are: 0.1 wt % for surfactant, 1 M for $CaCl_2$.

Visual assessments of 0.1 wt % solutions of C8, C12, and C14 sulfonate compositions of the invention, as produced in Examples 5, 7, and 8, in 10% sodium hydroxide, 1M calcium chloride, and at 7 degrees C. as compared to LAS and DOW-FAX™ 2A1 are shown in Table 2 below, and indicate that these new materials have desirable characteristics.

TABLE 2

|  | 0.1 wt % surfactant in 10% NaOH | 0.1 wt % surfactant in 1M CaCl2 | 1 wt % surfactant at 7° C. |
| --- | --- | --- | --- |
| C8 | clear | clear | clear |
| C12 | clear | clear | clear |
| C14 | clear | clear | clear |
| Dowfax ™ 2A1 | clear | clear | clear |
| LAS | cloudy | cloudy | cloudy |

Example 16

Aquatic Toxicity

The study procedures and test methods are based on the recommendations of the following guidelines:

Organization for Economic Cooperation and Development (OECD): OECD Guidelines for the Testing of Chemicals, "Freshwater Alga and Cyanobacteria, Growth Inhibition Test", Procedure 201, adopted 23 Mar. 2006; European Economic Community (EEC): Commission directive 92/69/EEC of 31 Jul. 1992, Methods for the determination of ecotoxicity, C.3., "Algal Inhibition Test".

Data from the aquatic toxicity tests of the isolated and purified C12 mono and disulfonates from Example 11 is shown in Table 3.

TABLE 3

| Aquatic toxicity results. | | |
| --- | --- | --- |
| Compound | Fresh Water algal growth inhibition test with *Desmondesmus subspicatus* ErC50/0-3 | 48-hour Acute Toxicity to *Daphna magna* (EC50) |
| Example 11 sodium 2-(dodecanyloxy)-3-hydroxypropane-1-sulfonate | >100 mg/l | >100 mg/l |
| Example 11 sodium 2-(dodecanyloxy) propane-1,3-disulfonate | >100 mg/l | >100 mg/l |

Toxicity is reported in accordance with the categorization system used by US EPA: Very toxic ($EC_{50}$</=0.1 mg/l); highly toxic ($EC_{50}$>0.1 and </=1 mg/l); moderately toxic ($EC_{50}$>1 and </=10 mg/l); slightly toxic ($EC_{50}$>10 and </=100 mg/l); practically non-toxic ($EC_{50}$>100 mg/l). The data shows that surfactants of the invention have highly favorable toxicity profiles.

Example 17

Evaluation of Cleaning Efficiency and Solubility

In this Example, the formulations shown in Table 4 are tested.

TABLE 4

|  | Formulation 1 (comparative) | Formulation 2 (inventive) |
| --- | --- | --- |
| Sodium Dodecylbenzene Sulfonate | 20% |  |
| (hexadecyl-2-yloxy)propane-1,3-disulfonate | 0 | 10% |
| (hexadecyl-2-yloxy)-3-hydroxypropane-1-sulfonate | 0 | 10% |
| ECOSURF ™ SA-7* | 2 | 2 |
| $C_{12-15}$ $EO_3$ (CAS 68131-39-5) | 2 | 2 |
| VERSENE 100** | 1 | 1 |
| ACUSOL 445N*** | 2 | 2 |
| $H_2O$ | to 100% | To 100% |

*ECOSURF SA-7 is a proprietary composition containing 2 alcohols alkoxylates manufactured by The Dow Chemical Company
**VERSENE 100 = A 40% active aqueous solution of $Na_4$ EDTA, a commercial product manufactured by The Dow Chemical Company
***ACUSOL 445N Acrylic Polymer with molecular weight of 4500 manufactured by Rohm and Haas a Wholly Owned subsidiary of The Dow Chemical Company "Cotton 400" swatches from Scientific Services S/D, Inc. stained with cooking grease and sudan red, Lot #1276, a standard soil in the industry, are independently washed with aqueous solutions of the two laundry formulations shown in Table 4.

Figure 5:
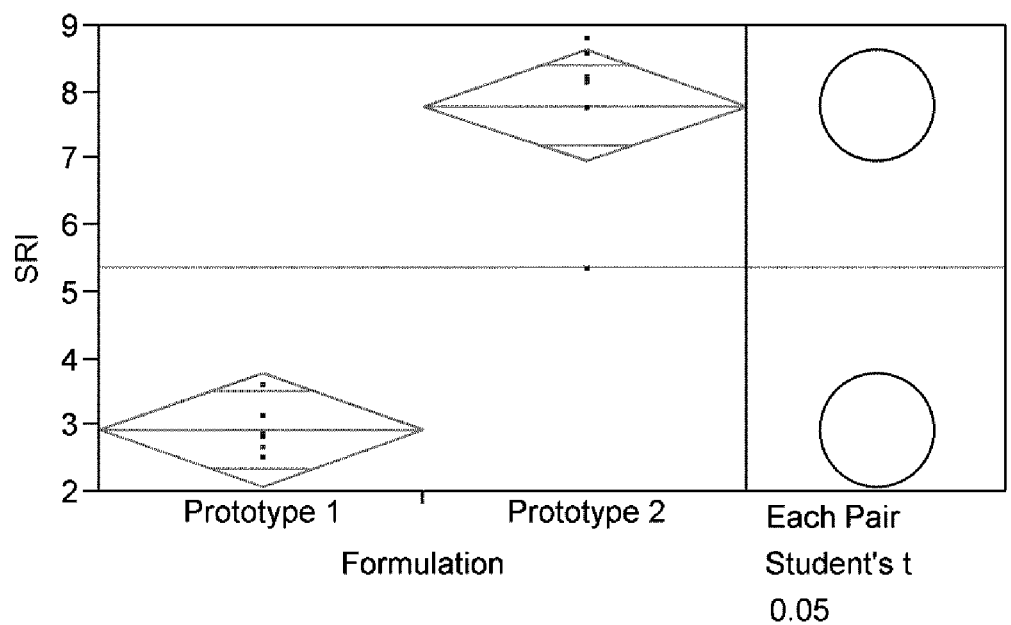
FIG. 5 is a graph comparing cleaning efficiency of an inventive formulation with a comparative formulation.

The procedure used for the evaluation is as follows:

A Tergitometer is used to carry out the washing. (A tergitometer is an industry standard equipment to run laundry on a laboratory scale). The tergitometer is set to run at 100 rpm. Each laundry pot contains 1 liter of total solution (water+formulation) and six swatches. Formulations are diluted at 2500 ppm in hard water immediately before the washing. The pH of the washing solution is adjusted to 10 with a diluted solution of NaOH. The hard water is prepared by diluting 1.37 g of CaCl2.2H2O and 0.43 g of MgCl2.6H2O in 4 liters of deionized water. Washing is carried out at 23° C. Washing Time is 25 minutes. Rinsing Time is 2 minutes in deionized water Cleaning efficiency (Stain Removal Index) is calculated based on the measurements of L, a*, b* color parameters of the swatches, according to the following equation:

$$SRI=[(L_1-L_2)^2+(a^*_1-a^*_2)^2+(b^*_1-b^*_2)^2]^{1/2}$$

where $X_1$=(L, a*, b*) parameters before laundry is carried out
where $X_2$=(L, a*, b*) parameters after laundry is carried out FIG. 5 is a graph showing a comparison of SRI for formulations 1 and 2. The data shows that inventive formulation 2 exhibits superior performance on grease removal than comparative formulation 1.

In addition to cleaning efficiency, the two formulations are also observed for solubility issues in the presence of calcium ions. Visual inspection shows that comparative formulation 1 exhibits the expected turbidity caused by the insolubility of calcium salts of the monosulfonate anionic surfactant, whereas inventive formulation 2, containing monosulfonate and disulfonate compounds of the invention, is clear and no insoluble salt is formed.

In addition to the visual inspection, digital analysis is carried out on images of the experimental solutions using imageJ software to measure the grey value of the images. Comparative formulation 1 exhibits a grey value of 19 whereas inventive formulation 2 exhibits a grey value of 9. This result confirms that insoluble salts are formed to a much greater extent for formulation 1 than for formulation 2.

Example 18

Emulsion Polymerization of Styrene-Butadiene Copolymer

A C12 sulfonate composition (of the invention), as prepared in Example 7, is tested in the emulsion polymerization of a styrene-butadiene copolymer and compared to a polymerization utilizing Dowfax™ 2A1 as surfactant. The following styrene-butadiene protocol is used. 0.454 parts seeded latex, 79.2 parts water, 36.5 parts butadiene, 28.3 parts styrene, 1 part t-dodecyl mercaptan are charged to a reactor. Into the reactor is further added 30.2 parts styrene, 5 parts acrylic acid, 15 parts water, 1 part sodium persulfate, 0.3 part C12 sulfonate composition of the invention (vs. 0.5 part Dowfax™ 2A1), and 0.1 part sodium hydroxide. Results of the analysis of the polymer made with the inventive C12 sulfonates surfactant, neutralized with sodium hydroxide to pH 6.2, are as follows:
Residue levels observed after filtration of the reactor over 100 and 325 mesh sieves: 26 mg/L. Solids: 50.9%. Particle size: 130 nm. Stability during polymerization and steam stripping: Excellent. Polymer Emulsion Surface Tension (1%): 48.6 dyn/cm at 25 degrees C. Ca2+ ion stability (determined by adding 10% calcium chloride solution to the latex until flocculation): 16 ml/100 g.

The surfactant of the invention provides excellent stability as indicated by the low residue levels observed after filtration of the reactor over 100 and 325 mesh sieves. The surfactant does not interfere with the particle size control. Similar particle size to the reference latexes (made with the Dowfax™ 2A1) is observed, indicating good stability during the polymerization and the steam stripping process. No significant difference in particle size distribution is observed. The surfactant does not impact the monomer conversion, as indicated by the residual styrene amount in the reactor sample. Similar glass transition temperatures and gel content are observed between polymers made with the inventive surfactant and those made with the comparative Dowfax™ 2A1. The carboxylic acid monomers are distributed between the serum phase, the latex particle surface or buried inside the polymer particles. There is no difference in acid distribution when changing the surfactant type.

The C12 sulfonate surfactant has no negative impact on reaction kinetic and particle size control. Similar latex and polymer properties are achieved when the amount of surfactant in the recipe is lowered by 40% for the sulfonate composition of the invention compared to the commercial benchmark. The surfactant can be used alone or in combination with other surfactants (including non-ionic or sulfated alkyl ethoxylate).

Example 19

Further Comparison of Surfactant Solubility

In this example, anionic surfactants of the invention are compared to non-inventive alkyl glyceryl ether sulfonate (AGS) surfactants. For purposes of the comparison, the comparative surfactants are prepared by the process commonly used for making AGS surfactants (see, for example, U.S. Pat. No. 2,989,547, U.S. Pat. No. 4,976,953A, U.S. Pat. No. 5,246,613A, WO 1997040131A1, U.S. Pat. No. 4,917,823A, U.S. Pat. No. 5,062,973A, EP 717032A2, U.S. Pat. No. 4,954,281A). This process involves: a) reaction of an alcohol with epichlorohydrin to form an epoxy-compound of formula B, then b) sulfonation to form the hydroxy monosulfonate of formula C:

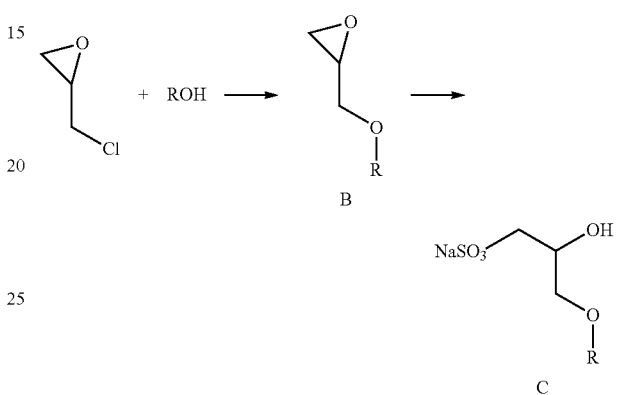

Aqueous solubilities of inventive surfactants and comparative (non-inventive) surfactants are shown in Table 5. The non-inventive surfactants show surprisingly low aqueous solubilities for R=C12 and R=C16 of Formula C, of <0.1 and <0.025 wt %, respectively. The low solubilities limits their utility as surfactant agents. By comparison, surfactant concentrations of greater than 9 and as high as 17 wt % with mixed branched alkyl chains of C8 to C12 sulfonate surfactants of the invention are observed.

TABLE 5

Solubility Assessment of AGS Surfactants

| R | Concentration (wt %) | Solubility in DI water |
|---|---|---|
| C16 (linear)* | 0.025% | Hazy |
| C12 (linear)* | 0.1% | Hazy |
| C12 (mixed branched) | 9.2% | Soluble |
| C8 (linear)* | 8.6% | Soluble |
| C8 (branched) 2-ethylhexyl | 17% | Soluble |

*comparative surfactant in which the ether is linked at the 1-position of the alkyl R group.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A compound of the formula I:

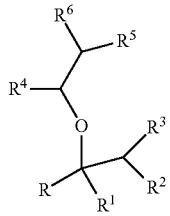

(I)

wherein R is linear or branched $C_2$-$C_{22}$ alkyl;
$R^1$, $R^2$, and $R^3$ are independently H or linear or branched $C_1$-$C_{18}$ alkyl;
$R^4$ is $CH_2SO_3^-M^+$, or $CH_2OH$;
$R^5$ is $SO_3^-M^+$;
$R^6$ is H; and
$M^+$ is $H^+$, or a monovalent or divalent cation.

2. The compound of claim 1 wherein R is linear $C_4$-$C_{16}$ alkyl.

3. The compound of claim 1 wherein $R^1$, $R^2$, and $R^3$ are each H.

4. A compound according to claim 1 which is: sodium 2-hexan-2-yloxypropane-1,3-disulfonate; sodium 2-hexan-2-yloxy-3-hydroxypropane-1-sulfonate; sodium 2-octan-2-yloxypropane-1,3-disulfonate; sodium 2-octan-2-yloxy-3-hydroxypropane-1-sulfonate; sodium 2-decan-2-yloxypropane-1,3-disulfonate; sodium 2-decan-2-yloxy-3-hydroxypropane-1-sulfonate; sodium 2-dodecan-2-yloxypropane-1,3-disulfonate; sodium 2-dodecan-2-yloxy-3-hydroxypropane-1-sulfonate; sodium 2-tetradecan-2-yloxypropane-1,3-disulfonate; sodium 2-tetradecan-2-yloxy-3-hydroxypropane-1-sulfonate; sodium 2-hexadecan-2-yloxypropane-1,3-disulfonate; sodium 2-hexadecan-2-yloxy-3-hydroxypropane-1-sulfonate; sodium 2-octadecan-2-yloxypropane-1,3-disulfonate; sodium 2-octadecan-2-yloxy-3-hydroxypropane-1-sulfonate; or mixtures of two or more thereof.

5. A formulation selected from laundry detergents, paint and coatings formulations, emulsion polymerization agents or formulations, household and industrial cleaners, agricultural formulations, latex formulations, environmental remediation agents, oilfield chemicals, enhanced oil recovery formulations, gas treating formulations, textile processing and finishing agents, pulp and paper processing agents, fragrance solubilization agents formulations, metal working fluids such as cutting fluids, and personal care products, comprising a compound according to claim 1 or a mixture of two or more thereof.

6. A laundry composition comprising a compound according to claim 1 or a mixture of two or more thereof.

7. The laundry composition of claim 6 further comprising one or more additional additives selected from: other anionic surfactants, non ionic surfactants, cationic surfactants, amphoteric surfactants, enzymes, solvents, hydrotropes, builders, thickening agents, chelating agents, perfume, dyes, opacifiers, optical brighteners, bleaching agents, and pH buffers.

8. A process for making the compound of claim 1, the process comprising:
(a) providing an ether compound of formula B:

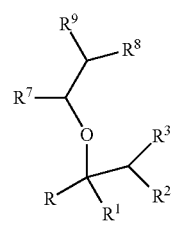

(B)

wherein R, $R^1$, $R^2$, and $R^3$ are as defined in claim 1; and
$R^7$ is $CH_2X$, $R^8$ is X, and $R^9$ is H; and
X is F, Cl, Br, or I; and
(b) sulfonating the ether compound of formula B under sulfonating conditions to provide the compound of claim 1.

9. A composition comprising two or more compounds according to claim 1.

* * * * *